US012646351B2

(12) United States Patent
Liu et al.

(10) Patent No.: US 12,646,351 B2
(45) Date of Patent: Jun. 2, 2026

(54) HUMAN FALLING DETECTION EMPLOYING THERMAL SENSOR AND IMAGE SENSOR

(71) Applicant: PixArt Imaging Inc., Hsin-Chu County (TW)

(72) Inventors: Feng-Chi Liu, Hsin-Chu County (TW); Nien-Tse Chen, Hsin-Chu County (TW)

(73) Assignee: PixArt Imaging Inc., Hsin-Chu County (TW)

( * ) Notice: Subject to any disclaimer, the term of this patent is extended or adjusted under 35 U.S.C. 154(b) by 388 days.

(21) Appl. No.: 17/963,533

(22) Filed: Oct. 11, 2022

(65) Prior Publication Data

US 2023/0033053 A1    Feb. 2, 2023

Related U.S. Application Data

(60) Continuation-in-part of application No. 17/470,358, filed on Sep. 9, 2021, now Pat. No. 11,615,642, which (Continued)

(51) Int. Cl.
*G06K 9/00*          (2022.01)
*A61B 5/00*          (2006.01)
(Continued)

(52) U.S. Cl.
CPC .......... *G06V 40/161* (2022.01); *A61B 5/0008* (2013.01); *A61B 5/0077* (2013.01);
(Continued)

(58) Field of Classification Search
None
See application file for complete search history.

(56) References Cited

U.S. PATENT DOCUMENTS 1,176,354 A      3/1916   Drake
5,689,241 A  *  11/1997   Clarke, Sr. ............. G08B 21/06
                                                          340/576

(Continued)

FOREIGN PATENT DOCUMENTS

CN          105956520 A      9/2016
CN          107084795 A      8/2017
(Continued)

OTHER PUBLICATIONS

Chen et al., "A Sensor Fusion Based Pan-Tilt Platform for Activity Tracking and Fall Detection." In Smart Materials, Adaptive Structures and Intelligent Systems, vol. 58264, p. V002T05A005. American Society of Mechanical Engineers, 2017. (Year: 2017).*

(Continued)

*Primary Examiner* — Feng Niu
(74) *Attorney, Agent, or Firm* — HAUPTMAN HAM, LLP

(57) ABSTRACT

There is provided a human falling detection system including an image sensor, a thermal sensor and a microphone. The image sensor captures an image frame that is used to identify a face and a height-width ratio of a human image. The thermal sensor is used as a filter for filtering out a living body and captures a thermal image that is used to identify a height-width ratio of a human thermal image. The microphone records a time stamp of an abrupt sound appearing.

20 Claims, 7 Drawing Sheets

100

Related U.S. Application Data is a division of application No. 16/442,783, filed on Jun. 17, 2019, now Pat. No. 11,328,152.

(51) Int. Cl.

| | |
|---|---|
| *A61B 5/01* | (2006.01) |
| *A61B 5/11* | (2006.01) |
| *G01J 5/00* | (2022.01) |
| *G01J 5/02* | (2022.01) |
| *G01J 5/08* | (2022.01) |
| *G06F 18/22* | (2023.01) |
| *G06F 18/25* | (2023.01) |
| *G06F 21/32* | (2013.01) |
| *G06V 10/143* | (2022.01) |
| *G06V 10/74* | (2022.01) |
| *G06V 10/80* | (2022.01) |
| *G06V 20/52* | (2022.01) |
| *G06V 40/10* | (2022.01) |
| *G06V 40/16* | (2022.01) |
| *G06V 40/20* | (2022.01) |
| *G06V 40/40* | (2022.01) |

(52) U.S. Cl.
CPC .............. *A61B 5/01* (2013.01); *A61B 5/1117* (2013.01); *A61B 5/1128* (2013.01); *A61B 5/742* (2013.01); *A61B 5/746* (2013.01); *G01J 5/0025* (2013.01); *G01J 5/026* (2013.01); *G01J 5/0846* (2013.01); *G01J 5/0859* (2013.01); *G06F 18/22* (2023.01); *G06F 18/251* (2023.01); *G06F 21/32* (2013.01); *G06V 10/143* (2022.01); *G06V 10/761* (2022.01); *G06V 10/803* (2022.01); *G06V 20/52* (2022.01); *G06V 40/103* (2022.01); *G06V 40/168* (2022.01); *G06V 40/172* (2022.01); *G06V 40/20* (2022.01); *G06V 40/28* (2022.01); *A61B 5/015* (2013.01); *G01J 2005/0077* (2013.01); *G06V 40/117* (2022.01); *G06V 40/16* (2022.01); *G06V 40/45* (2022.01)

(56) References Cited

U.S. PATENT DOCUMENTS

| | | | |
|---|---|---|---|
| 6,529,617 B1* | 3/2003 | Prokoski .............. A61B 5/1171 | |
| | | | 382/128 |
| 6,542,849 B2* | 4/2003 | Sun ........................ G01B 11/06 | |
| | | | 702/170 |
| 7,555,437 B2 | 6/2009 | Pierce | |
| 8,233,047 B2 | 7/2012 | Shimbo et al. | |
| 8,463,006 B2* | 6/2013 | Prokoski .............. G06T 7/0012 | |
| | | | 382/128 |
| 8,494,227 B2* | 7/2013 | Prokoski .............. G06T 7/0012 | |
| | | | 382/270 |
| 9,245,196 B2 | 1/2016 | Marks | |
| 9,529,513 B2 | 12/2016 | Balan et al. | |
| 9,603,566 B2 | 3/2017 | Chen | |
| 9,928,413 B2 | 3/2018 | Baca et al. | |
| 10,029,047 B2 | 7/2018 | Gupta et al. | |
| 10,074,028 B2 | 9/2018 | Gupta | |
| 10,194,138 B2 | 1/2019 | Zhou | |
| 10,383,604 B2* | 8/2019 | Pardey ................. A61B 5/7278 | |
| 10,471,552 B2* | 11/2019 | Raulerson ............... F01D 25/12 | |
| 10,650,036 B2 | 5/2020 | Kimura et al. | |
| 10,664,215 B2 | 5/2020 | Aurongzeb | |
| 10,678,901 B2* | 6/2020 | Shoenfeld ............. A61B 50/13 | |
| 10,691,943 B1 | 6/2020 | Ferstl et al. | |
| 10,795,508 B2 | 10/2020 | Han | |
| 10,802,596 B2 | 10/2020 | Cao | |
| 10,970,373 B2 | 4/2021 | Lee et al. | |
| 11,157,605 B2 | 10/2021 | Guo et al. | |
| 11,176,354 B2 | 11/2021 | Lin | |

| | | | |
|---|---|---|---|
| 11,238,979 B1 | 2/2022 | Schilling | |
| 11,253,207 B2* | 2/2022 | Shah ........................ A61B 5/747 | |
| 11,291,401 B2 | 4/2022 | Velo | |
| 11,328,152 B2 | 5/2022 | Chen et al. | |
| 11,350,167 B2* | 5/2022 | Lee .................... H04N 21/4667 | |
| 11,484,232 B2* | 11/2022 | Harley-Trochimczyk .................. | |
| | | | A61B 5/14532 |
| 11,606,493 B2* | 3/2023 | Mishra .................. H04N 5/783 | |
| 11,615,642 B2 | 3/2023 | Chen et al. | |
| 11,615,871 B2 | 3/2023 | Gupta et al. | |
| 11,789,527 B1* | 10/2023 | Bilous ..................... G06F 3/012 | |
| | | | 345/633 |
| 2002/0128797 A1* | 9/2002 | Sun ......................... G01B 11/22 | |
| | | | 702/172 |
| 2005/0200486 A1 | 9/2005 | Greer | |
| 2007/0150026 A1* | 6/2007 | Bourget ............. A61N 1/37252 | |
| | | | 607/46 |
| 2007/0159332 A1 | 7/2007 | Koblasz | |
| 2008/0065291 A1 | 3/2008 | Reed | |
| 2010/0172567 A1* | 7/2010 | Prokoski ................. A61B 5/418 | |
| | | | 348/47 |
| 2010/0189313 A1* | 7/2010 | Prokoski ................. A61B 5/015 | |
| | | | 382/118 |
| 2011/0066010 A1 | 3/2011 | Moon | |
| 2012/0029308 A1* | 2/2012 | Paquet ..................... A61B 5/01 | |
| | | | 600/549 |
| 2012/0029312 A1 | 2/2012 | Beaudry | |
| 2012/0127306 A1 | 5/2012 | Oh | |
| 2013/0212633 A1 | 8/2013 | Emerson | |
| 2013/0281883 A1 | 10/2013 | Nishida | |
| 2013/0342691 A1 | 12/2013 | Lewis et al. | |
| 2015/0040040 A1 | 2/2015 | Balan et al. | |
| 2015/0305632 A1* | 10/2015 | Najarian .............. A61B 5/7207 | |
| | | | 600/479 |
| 2015/0323388 A1 | 11/2015 | Kostic et al. | |
| 2015/0373307 A1 | 12/2015 | Huang et al. | |
| 2016/0034747 A1 | 2/2016 | Jo et al. | |
| 2016/0143630 A1* | 5/2016 | Pardey ..................... A61B 5/01 | |
| | | | 600/549 |
| 2016/0162039 A1 | 6/2016 | Eilat et al. | |
| 2016/0318135 A1* | 11/2016 | Raulerson .............. B23P 6/002 | |
| 2018/0075032 A1 | 3/2018 | Kimura et al. | |
| 2018/0128691 A1 | 5/2018 | Ou Yang | |
| 2018/0132735 A1* | 5/2018 | Weebadde ........... A61B 5/0006 | |
| 2018/0189547 A1 | 7/2018 | Daniels et al. | |
| 2018/0218371 A1* | 8/2018 | Wang ..................... G06V 40/16 | |
| 2018/0235468 A1 | 8/2018 | Khachaturian | |
| 2018/0357886 A1 | 12/2018 | Tavori | |
| 2019/0011702 A1 | 1/2019 | Zhang | |
| 2019/0110692 A1 | 4/2019 | Pardey | |
| 2019/0159739 A1 | 5/2019 | Shah | |
| 2019/0167237 A1 | 6/2019 | Stein | |
| 2019/0227022 A1* | 7/2019 | Harley-Trochimczyk .................. | |
| | | | A61B 5/14532 |
| 2019/0287376 A1 | 9/2019 | Netscher | |
| 2019/0357891 A1* | 11/2019 | Pardey ............... A61B 5/7282 | |
| 2019/0384407 A1 | 12/2019 | Smith et al. | |
| 2020/0042683 A1 | 2/2020 | Lee et al. | |
| 2020/0159368 A1 | 5/2020 | Han et al. | |
| 2020/0160081 A1 | 5/2020 | Nakamura et al. | |
| 2020/0218794 A1 | 7/2020 | Zheng | |
| 2020/0238952 A1 | 7/2020 | Lindsay et al. | |
| 2020/0374465 A1 | 11/2020 | Kimura | |
| 2020/0410274 A1 | 12/2020 | Satoh | |
| 2021/0092486 A1* | 3/2021 | Lee .................... H04N 21/4532 | |
| 2021/0244286 A1* | 8/2021 | Pardey ................. A61B 5/4325 | |
| 2021/0294482 A1 | 9/2021 | Ikeda et al. | |
| 2021/0397817 A1 | 12/2021 | Su et al. | |
| 2021/0401291 A1 | 12/2021 | Schriek et al. | |
| 2023/0027040 A1 | 1/2023 | Wang et al. | |
| 2023/0134325 A1* | 5/2023 | Bevan ..................... A61B 5/015 | |
| | | | 600/474 |
| 2024/0036639 A1* | 2/2024 | Bilous ..................... G06F 3/012 | |

FOREIGN PATENT DOCUMENTS

| | | |
|---|---|---|
| CN | 108416968 A | 8/2018 |
| CN | 109377628 A | 2/2019 |

(56) References Cited

FOREIGN PATENT DOCUMENTS

| | | | | |
|---|---|---|---|---|
| CN | 112101216 A | | 12/2020 | |
| JP | 2015161476 A | * | 9/2015 | .............. F25D 11/00 |
| JP | 2019010927 A | | 1/2019 | |
| WO | 2008066130 A1 | | 6/2008 | |

OTHER PUBLICATIONS

Mubashir et al., "A survey on fall detection: Principles and approaches." Neurocomputing 100 (2013): 144-152. (Year: 2013).*

Miaou et al., "A customized human fall detection system using omni-camera images and personal information." In 1st Transdisciplinary Conference on Distributed Diagnosis and Home Healthcare, 2006. D2H2., pp. 39-42. IEEE, 2006. (Year: 2006).*

Toreyin et al., "Falling person detection using multi-sensor signal processing." EURASIP Journal on Advances in Signal Processing 2008 (2007): 1-7. (Year: 2007).*

Liu et al., "Automatic Fall Risk Detection Based on Imbalanced Data," in IEEE Access, vol. 9, pp. 163594-163611, 2021 (Year: 2021).*

Vallabh et al., "Fall detection monitoring systems: a comprehensive review." J Ambient Intell Human Comput 9, 1809-1833 (2018). (Year: 2018).*

JP-2015161476-A (machine translation) (Year: 2015).*

Marrin et al., "A meta-analytic approach to quantify the dose-response relationship between melatonin and core temperature." European Journal of Applied Physiology 113 (2013): 2323-2329. (Year:2013).

Renevey et al., "Photoplethysmography-Based Bracelet for Automatic Sleep Stages Classification: Preliminary Results", Iasted 2014, Zurich, Switzerland (Year: 2014).

* cited by examiner

100

400

HUMAN FALLING DETECTION EMPLOYING THERMAL SENSOR AND IMAGE SENSOR

CROSS REFERENCE TO RELATED APPLICATION

The present application is a continuation-in-part application of U.S. patent application Ser. No. 17/470,358 filed on, Sep. 9, 2021, which a divisional application of U.S. application Ser. No. 16/442,783, filed on Jun. 17, 2019, the disclosures of which are hereby incorporated by reference herein in their entirety.

BACKGROUND

1. Field of the Disclosure

This disclosure generally relates to a recognition system and device and, more particularly, to a recognition system and device that use a thermal sensor to implement functions including the living body recognition, image denoising and body temperature monitoring.

2. Description of the Related Art

The image sensor has been broadly adapted to portable devices as an unlocking means. However, it is difficult to directly use an image sensor to identify a living body in some scenarios, and the image sensor further has a problem of being easily affected by ambient light. In order to solve these issues, a complicated algorithm generally has to be used.

In addition, due to the population aging, the burden for elder and infant nursing to the society gradually becomes heavier. It is not possible to fully rely on human to do the nursing since there is no longer enough manpower, the technology must be used to implement the automatic monitoring thereby reducing the manpower requirement and society cost.

Accordingly, the present disclosure provides a recognition system that adopts a temperature sensor to compensate the insufficiency of a system that uses only an image sensor.

SUMMARY

The present disclosure provides a falling detection system employing an image sensor, a thermal sensor and a microphone.

The present disclosure provides a falling detection system including an image sensor, a single-pixel thermal sensor, a microphone and a processor. The image sensor is configured to output an image frame. The single-pixel thermal sensor is configured to output a thermal signal. The microphone is configured to output a voice signal. The processor is coupled to the image sensor, the single-pixel thermal sensor and the microphone, and configured to identify an object of interest according to at least one of face recognition and a height-width ratio of an object image in the image frame, identify whether the object of interest is a living body or not according to the thermal signal, identify a height-width ratio change of the object of interest upon the object of interest being identified as the living body, and identify whether a time stamp of the height-width ratio change matches an abrupt sound in the voice signal.

The present disclosure further provides a falling detection system including an image sensor, a thermal sensor array, a microphone and a processor. The image sensor is configured to output an image frame. The thermal sensor array is configured to output a thermal image. The microphone is configured to output a voice signal. The processor is coupled to the image sensor, the thermal sensor array and the microphone, and configured to identify an object of interest according to at least one of face recognition of an object image in the image frame and a height-width ratio of a thermal object image in the thermal image corresponding to the object image, identify whether the object of interest is a living body or not according to the thermal object image in the thermal image, identify a height-width ratio change of the thermal object image in the thermal image associated with the object of interest upon the object of interest being identified as the living body, and identify whether a time stamp of the height-width ratio change matches an abrupt sound in the voice signal.

The present disclosure provides a falling detection system including an image sensor, a thermal sensor array, a microphone and a processor. The image sensor is configured to output an image frame. The thermal sensor array is configured to output a thermal image. The microphone is configured to output a voice signal. The processor is coupled to the image sensor, the thermal sensor array and the microphone, and configured to determine an object of interest when an object image in the image frame is identified as a living body according to a thermal object image in the thermal image corresponding to the object image, and identify a human falling event according to at least one of a face position change of the object image in successive image frames acquired by the image sensor and a height-width ratio change of the thermal object image in successive thermal images acquired by the thermal sensor array in conjunction with an abrupt sound in the voice signal.

In the present disclosure, the denoising method of the gesture recognition system is also adaptable to the face recognition system to improve the recognition accuracy of the system.

BRIEF DESCRIPTION OF THE DRAWINGS

Other objects, advantages, and novel features of the present disclosure will become more apparent from the following detailed description when taken in conjunction with the accompanying drawings.

DETAILED DESCRIPTION OF THE EMBODIMENT

It should be noted that, wherever possible, the same reference numbers will be used throughout the drawings to refer to the same or like parts.

Figure 1:
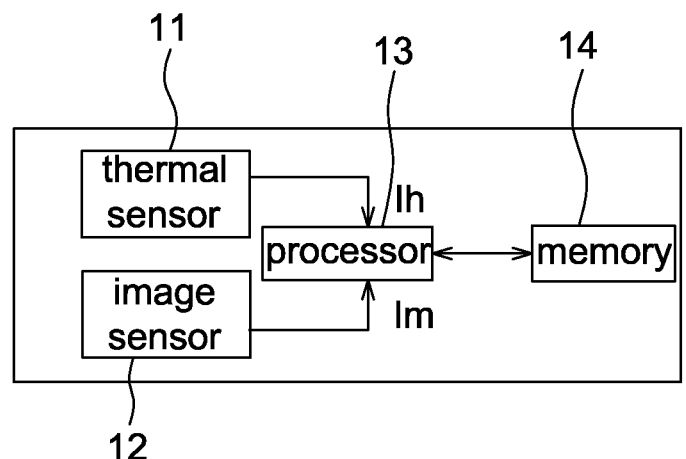
FIG. 1 is a block diagram of a recognition system according to one embodiment of the present disclosure.

Referring to FIG. 1, it is a schematic block diagram of a recognition system 100 according to one embodiment of the present disclosure. The recognition system 100 is applicable to a portable device including electronic devices such as a cell phone, a tablet computer, a notebook computer or the like; and the recognition system 100 is also applicable to a wearable device including electronic devices such as a watch, a bracelet, an armband or the like, but not limited thereto. The recognition system 100 includes a thermal sensor 11, an image sensor 12, a processor 13 and a memory 14. The recognition system 100 performs at least the face recognition and the gesture recognition.

The thermal sensor 11 includes a Pyroelectric Infrared (PIR) type, a thermopile type or a bolometer type sensor, which is used to detect infrared light and output electrical signals (e.g., voltage or current signals) or digital signals to respond to detected temperatures. Preferably, the thermal sensor 11 outputs a two-dimensional thermal image to correspond to a two-dimensional (2D) image frame acquired by the image sensor 12. For example, a detected value of each pixel of the 2D thermal image indicates a temperature of a detected region, and the detected regions corresponding to adjacent pixels of the 2D thermal image are arranged to overlap partially or not overlapped with each other depending on the microlens arrangement thereupon.

Compared with the conventional temperature sensor that performs the thermal sensing or temperature sensing by contacting the object to be detected, the thermal sensor 11 of the present disclosure is capable of detecting the temperature by non-contacting with the object to be detected because the thermal sensor 11 can be a thermopile sensor or a bolometer sensor. In other words, the thermal sensor 11 of the present disclosure can detect the temperature of a target (e.g., human body) even though the target is covered by clothes or cloth thereby having higher reliability and applicability.

The image sensor 12 includes, for example, a CCD image sensor, a CMOS image sensor or the like, which has multiple pixels arranged in a matrix to output the 2D image frame.

The processor 13 is, for example, a digital signal processor (DSP), a microcontroller (MCU), a central processing unit (CPU), an application specific integrated circuit (ASIC), a graphic processing unit (GPU) or the like. The processor 13 is electrically coupled to the thermal sensor 11 and the image sensor 12 to respectively receive a thermal image Ih and an image frame Im for the post-processing by software and/or hardware. The processor 13 also controls ON/OFF of the thermal sensor 11 and the image sensor 12 as well as operation of pixels thereof.

The memory 14 includes, for example, a volatile memory and/or non-volatile memory. The memory 14 is used to previously record the algorithm, threshold(s) and parameter(s) used by the processor 13 in the post-processing. In different applications, the memory 14 further temporarily stores data of the thermal image Ih and/or the image frame Im detected during operation.

Figure 2A:
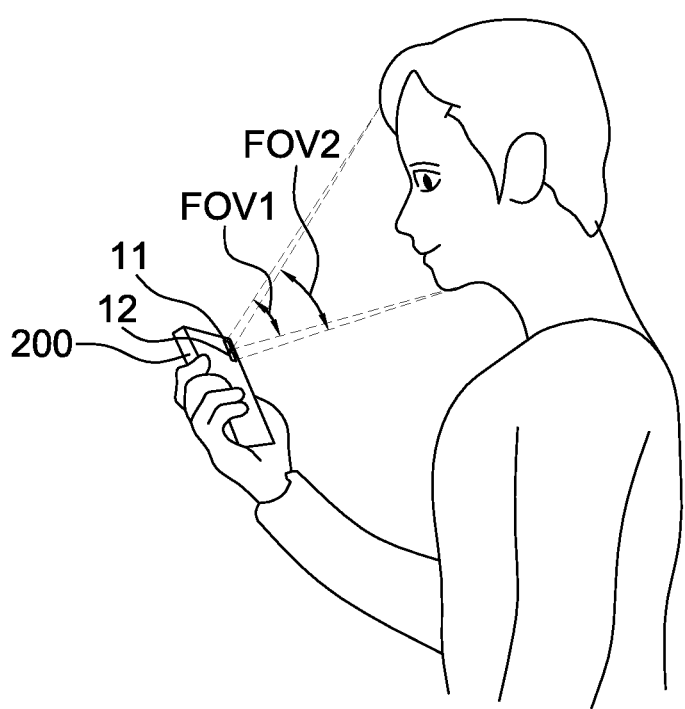
FIG. 2A is an operational schematic diagram of a face recognition system according to a first embodiment of the present disclosure.
Figure 2B:
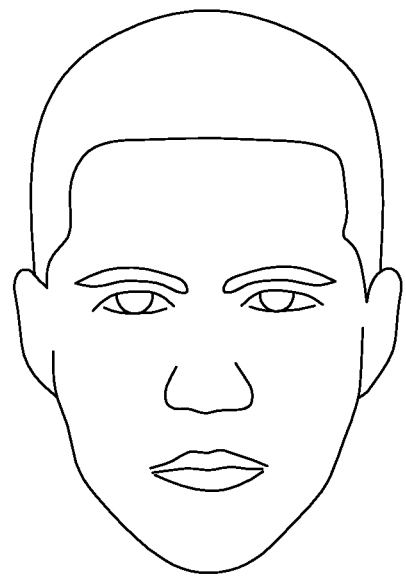
FIG. 2B is a schematic diagram of a face image acquired by a face recognition system according to a first embodiment of the present disclosure.
Figure 2C:
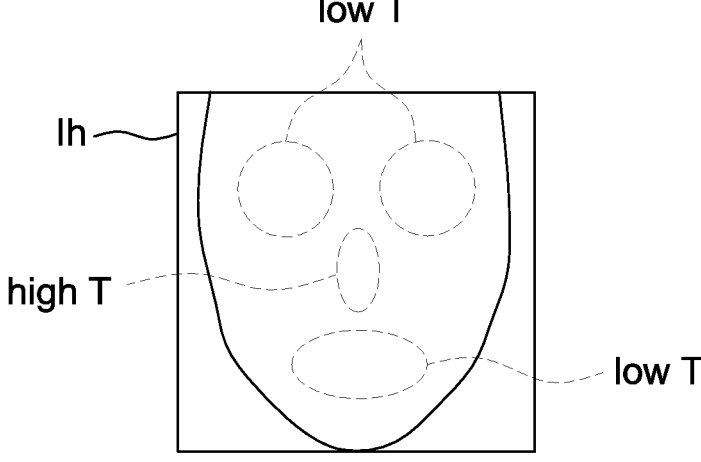
FIG. 2C is a schematic diagram of a temperature distribution of a thermal image acquired by a face recognition system according to a first embodiment of the present disclosure.

Referring to FIG. 2A, it is a schematic diagram of a face recognition system 200 according to a first embodiment of the present disclosure. FIG. 2A shows the face recognition system 200 being arranged close to the side of a portable device facing the user. The face recognition system 200 includes the thermal sensor 11, the image sensor 12, the processor 13 and the memory 14 shown in FIG. 1. The thermal sensor 11 acquires a thermal image Ih (e.g., FIG. 2C showing the temperature distribution thereof) with a first field of view FOV1, and the thermal image Ih is outputted to the processor 13. The image sensor 12 acquires an image frame Im (e.g., FIG. 2B showing a face image therein) with a second field of view FOV2, and the image frame Im is outputted to the processor 13. To acquire corresponding features, at least a part of FOV1 overlaps with FOV2 to acquire information of the same area or surface using different sensors. The thermal sensor 11 and the image sensor 12 are arranged to simultaneously or alternatively acquire images without particular limitations.

The processor 13 performs the face recognition and/or the material recognition according to the image frame Im, wherein the processor 13 uses the conventional face recognition algorithm to recognize facial features of a face image (e.g., as shown in FIG. 2B), and uses the conventional material recognition algorithm to recognize skin material in the image frame Im. The processor 13 performs the living body recognition according to a regional heat distribution in the thermal image Ih corresponding to the facial features of the face image in the image frame Im.

In an image type unlocking system, to prevent an unregistered person from unlocking the system using a photo or video of a registered face, the face recognition system 200 of the first embodiment of the present disclosure distinguishes a fake according to the thermal image Ih captured by the thermal sensor 11 and the skin material of a face in the image frame Im. Accordingly, the living body herein is referred to a real person instead of a photo or video.

For example in one non-limiting aspect, the processor 13 does not turn on the thermal sensor 11 before identifying that a registered face image is contained in the image frame Im or the registered face image has skin material so as to reduce the power consumption, i.e. the processor 13 turning on the thermal sensor 11 only when a registered face image is identified in the image frame Im or the registered face image has skin material, but the present disclosure is not limited thereto.

In another non-limiting aspect, the processor 13 conversely controls the thermal sensor 11 and the image sensor 12. That is, the processor 13 does not turn on the image sensor 12 before an area of an object image in the thermal image Ih is identified to be larger than a threshold. The processor 13 turns on the image sensor 12 to perform the face recognition only when the thermal image Ih contains a valid face image (i.e. object area larger than the threshold). In other aspects, during the unlocking, the thermal sensor 11 and the image sensor 12 are both turned on or activated.

In the first embodiment, a range covered by a first field of view FOV1 of the thermal sensor 11 is preferably larger than a second field of view FOV2 of the image sensor 12. In addition, as the living body recognition is performed according to the thermal image Ih, the processor 13 only performs the 2D face recognition according to the image frame Im without performing the three-dimensional (3D) face recognition to reduce the power computation. Traditionally, the 3D face recognition can be used to distinguish a photo from a person, but higher calculation loading is required.

In addition, to further prevent an unregistered person to perform the unlocking using a heated photo, the processor 13 not only confirms whether an object image in the thermal image Ih has a temperature larger than a predetermined temperature, but also identifies a regional heat distribution in the thermal image Ih. For example referring to FIG. 2C, the thermal image Ih contains high and low temperature regions, e.g., a high temperature region corresponding to a nose area of the face image (as shown in FIG. 2B) in the image frame Im, and low temperature regions corresponding to eyes and mouth areas of the face image in the image frame Im.

In this case, the memory 14 previously records the temperature distribution of various face regions, which is stored in the memory 14 by detecting a registered user in a setting mode (e.g., entered by executing an application or pressing a key), or obtained by a statistical result which is stored in the memory 14 before shipment. The processor 13 compares (e.g., calculating similarity or correlation) the regional heat distribution in a current thermal image (e.g., a thermal image Ih acquired during the unlocking) with the pre-stored temperature distribution to perform the living body recognition. In addition, the processor 13 calculates a temperature difference between areas of the high and low temperature regions to confirm that an object currently being detected by the face recognition system 200 is indeed a human body rather than a fake.

In another aspect, the processor 13 compares the regional heat distribution in a current thermal image with locations of facial features (e.g., the eyes, nose and mouth) identified from the captured image frame Im to confirm whether the regional heat distribution matches with the corresponding facial features or not. In this way, it is also possible to distinguish a fake from a real human face without recording the temperature distribution previously in the memory 14.

After the confirmation of a registered face is accomplished through the face recognition, the processor 13 then turns on or activates operating functions of an electronic device that adopts the face recognition system 200, e.g., activating the display screen.

Figure 3A:
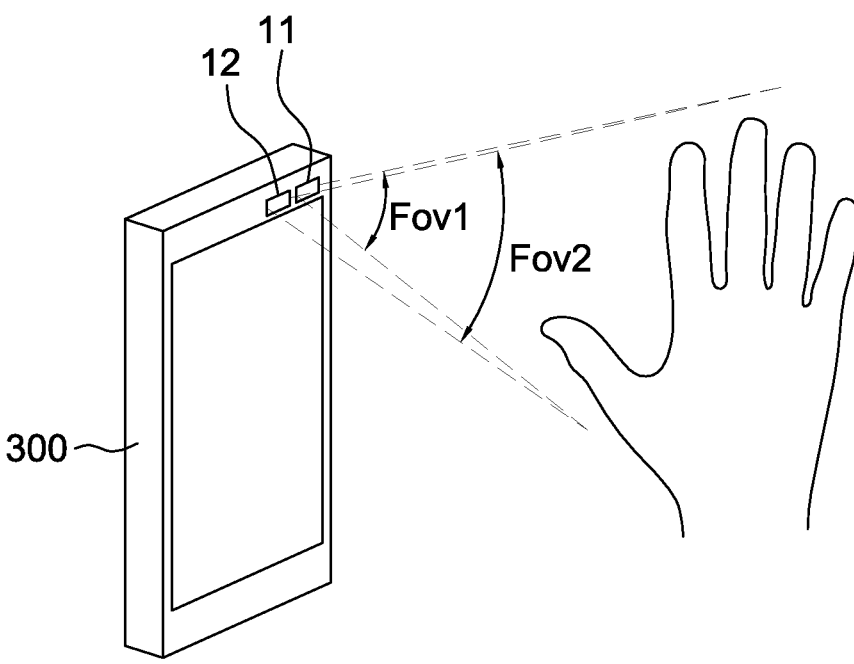
FIG. 3A is an operational schematic diagram of a gesture recognition system according to a second embodiment of the present disclosure.
Figure 3B:
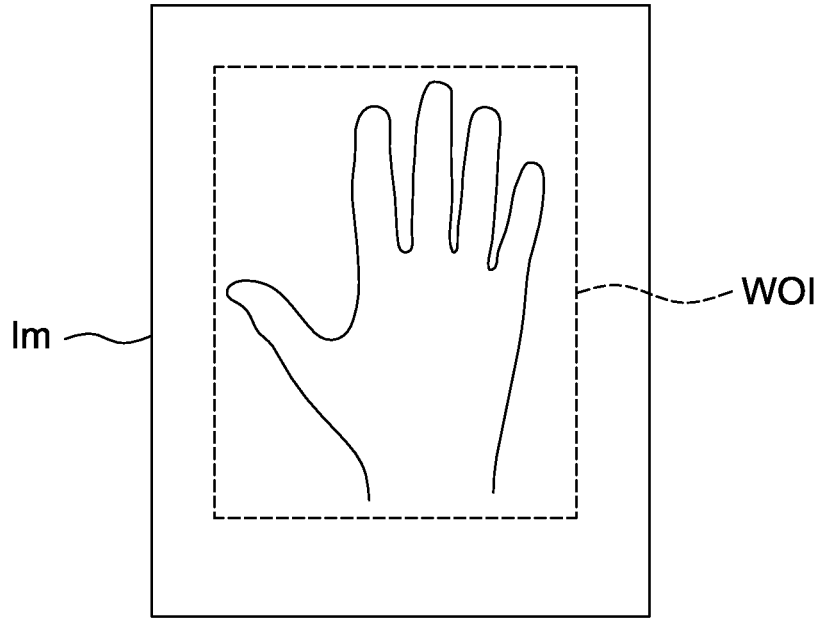
FIG. 3B is a schematic diagram of an image frame acquired by a gesture recognition system according to a second embodiment of the present disclosure.

Referring to FIG. 3A, it is a schematic diagram of a gesture recognition system 300 according to a second embodiment of the present disclosure. FIG. 3A shows the gesture recognition system 300 being arranged at the side of a portable device facing the user. The gesture recognition system 300 also includes the thermal sensor 11, the image sensor 12, the processor 13 and the memory 14 shown in FIG. 1. The thermal sensor 11 is used to acquire a thermal image Ih with a first field of view FOV1, and the thermal image Ih is outputted to the processor 13. The image sensor 12 is used to acquire an image frame Im (as shown in FIG. 3B) with a second field of view FOV2, and the image frame Im is also outputted to the processor 13.

The processor 13 determines a processed region WOI in the thermal image Ih, and performs the gesture recognition according to an image region in the image frame Im corresponding to the processed region WOI determined in the thermal image Ih so as to eliminate the interference from ambient light. Accordingly, to allow the processor 13 to be able to correctly determine the processed region WOI in the image frame Im, in the second embodiment the first field of view FOV1 of the thermal sensor 11 is preferable equal to the second field of view FOV2 of the image sensor 12, and sizes of the thermal image Ih and the image frame Im are preferable identical. For example, a corresponding processed region WOI in the image frame Im is obtained according to pixel addresses or pixel locations within the determined processed region WOI in the thermal image Ih.

For example, the processor 13 identifies a region in the thermal image Ih having a temperature larger than a temperature threshold (determined according to body temperature) as the processed region WOI, which is an image region in the thermal image Ih. As the second field of view FOV2 is arranged corresponding to the first field of view FOV1, the processor 13 confirms a corresponding processed region WOI in the image frame Im as shown in FIG. 3B, wherein a size of the corresponding processed region WOI is smaller than that of the image frame Im. It should be mentioned that the processed range WOI is not limited to a rectangle as shown in FIG. 3B but is another suitable shape as long as it covers the object region in the image frame Im. In some scenarios, two processed regions WOI are defined corresponding to two object regions.

In other aspects, the first field of view FOV1 and the second field of view FOV2 are not totally identical to each other and have an angle difference. In this case, the memory 14 previously stores a space conversion algorithm or matrix transformation algorithm between the thermal image Ih and the image frame Im. In this way, after confirming the processed region WOI in the thermal image Ih, the processor 13 confirms a corresponding processed region WOI in the image frame Im according to the stored algorithm.

In another non-limiting aspect, the processor 13 firstly identifies an object image in the image frame Im, which may also contain an image of ambient light. The processor 13 then removes the non-human image based on the thermal image Ih. For example, the object image outside the processed region WOI is not used in the gesture recognition so as to effectively improve the recognition accuracy and eliminate the interference.

More specifically, in the second embodiment, the processor 13 performs the gesture recognition according to a partial image of the image frame Im, and the thermal image Ih is for the denoising function.

In addition, in the low power consumption scenario, the processor 13 turns on the image sensor 12 only after identifying a processed region WOI in the thermal image Ih larger than a predetermined size. In this case, a whole sensor array of the image sensor 12 is turned on or a part of the sensor array corresponding to the WOI is turned on. In other words, when the thermal image Ih does not contain a region having a temperature higher than a predetermined temperature threshold, the processor 13 only turns on the thermal sensor 11 to capture thermal images Ih at a predetermined frequency; or, even though the thermal image Ih contains a region having a temperature higher than the predetermined temperature threshold, the processor 13 still only turns on the thermal sensor 11 to acquire thermal images Ih at a predetermined frequency if the region is smaller than a predetermined size, which is determined according to a hand size within a detectable distance of the system, but the present disclosure is not limited thereto.

In other aspects, during the gesture recognition, the thermal sensor 11 and the image sensor 12 are both turned on or activated. For example, only a part of pixels of the thermal sensor 11 are turned on, and said the part of pixels corresponds to a pixel region of the image sensor 12 detecting an object. More specifically, in the present disclosure sensor arrays of the thermal sensor 11 and the image sensor 12 are not necessary to be fully turned on but only a part of pixels thereof are turned on to reduce the power consumption.

In an alternative embodiment, the processor 13 performs a material recognition in the image frame Im captured by the image sensor 11 at first and then performs the gesture recognition according to the thermal image Ih captured by the thermal sensor 11. For example, if an object image in the image frame Im is not identified to have skin material by the processor 13, the thermal sensor 11 is not turned on. The thermal sensor 11 is turned on only when a skin material is identified in the image frame Im. Furthermore, the processor 13 also determines a WOI in the thermal image Ih based on a skin material region in the image frame Im, i.e., the processor 13 firstly determining a skin material region in the image frame Im at first and then determining a WOI in the thermal image Ih corresponding to the skin material region. The gesture recognition is performed using the object image only within the WOI in the thermal image Ih.

It should be mentioned that although in the above first and second embodiments the recognition system 100 is illustrated by applying to a portable device, the present disclosure is not limited thereto. The recognition system 100 of the first and second embodiments is also applicable to a wearable device, the security system and/or control system of a gate or a vehicle. The processor 13 performs the living body recognition and denoising using the thermal image Ih to improve the identification accuracy and security.

Figure 4:
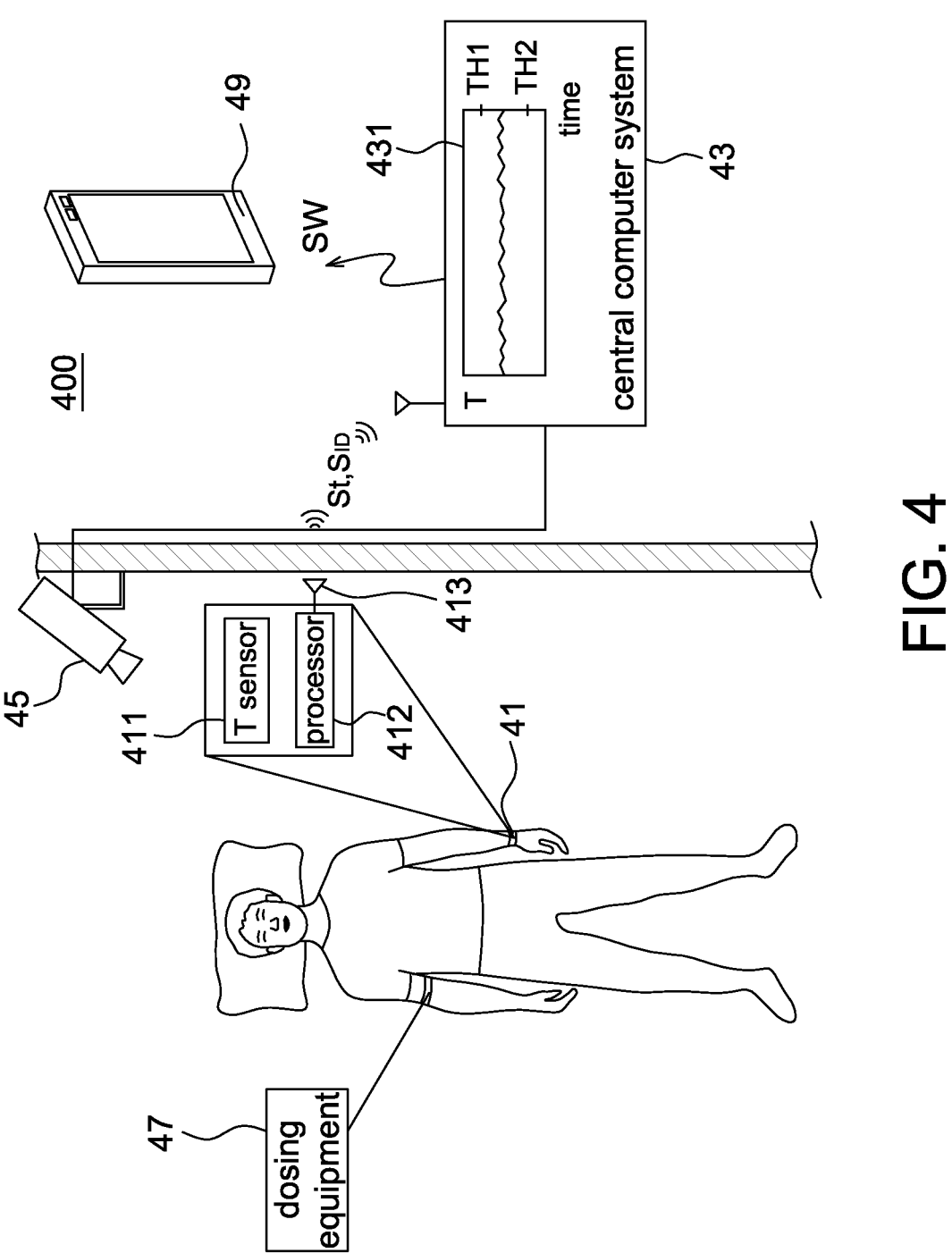
FIG. 4 is a schematic diagram of a medical monitoring system according to a third embodiment of the present disclosure.

Please referring to FIG. 4, it is a schematic diagram of a medical monitoring system 400 according to a third embodiment of the prevent disclosure. The medical monitoring system 400 is applied to a medical institute or a care institute so as to solve the problem caused by the manpower shortage. The medical monitoring system 400 mainly includes a wearable accessory 41 and a central computer system 43 coupled to each other. The wearable accessory 41 is worn on a human body, e.g., FIG. 4 showing on a human arm, but not limited thereto. The wearable accessory 41 is worn on any body part suitable for measuring the body temperature. The central computer system 43 performs a corresponding response, e.g., providing a warning, according to detected results of the wearable accessory 41.

For example, the wearable accessory 41 is a customized accessory, a smart watch, a smart armband, a smart bracelet or the like. The wearable accessory 41 at least includes a thermal sensor (shown as T sensor) 411, a processor 412 and a transmitter 413. The thermal sensor 411 is similar to that in the first and second embodiments for outputting a 2D thermal image, and the processor 412 calculates an average temperature of the 2D thermal image. Besides, in the third embodiment, the thermal sensor 411 includes one sensing unit (e.g., photodiode) and outputs one electrical signal or digital signal at a time to indicate a detected temperature instead of outputting a 2D thermal image. The processor 412 is also a DSP, MCU, CPU, ASIC, GPU or the like.

In the case that the thermal sensor 411 is embedded in other electronic devices not directly contact a user (e.g., the electronic device arranged at the wall or ceiling), the thermal sensor 411 monitors temperature of the whole body of the user. The electronic device provides a warning message St if a temperature difference between the core temperature and limb temperature is larger than a predetermined threshold.

In measuring body temperature, the thermal sensor 411 directly detects a temperature of a skin surface as the body temperature, or detects a temperature difference between the room temperature and the body temperature (i.e. the room temperature and the body temperature being detected simultaneously using identical or different sensors) and obtains the body temperature by subtracting (using the processor 412) the temperature difference from the room temperature.

The thermal sensor 411 is used to detect a body temperature and output an electrical signal or a digital signal to the processor 412. The processor 412 identifies a temperature according to the received signal, and then controls the transmitter 413 (shown by an antenna in FIG. 4) to send a temperature message St associated with the body temperature and a label message $S_{ID}$ of the wearable accessory 41 (e.g., the medical monitoring system 400 including multiple wearable accessories 41 each having an individual label) in a wireless manner such as the Bluetooth communication, Zigbee, microwave communication, but not limited to.

In one aspect, the central computer system 43 is arranged at a suitable location capable of receiving the temperature message St and the label message $S_{ID}$, and used to store the received temperature message St onto cloud or in a memory therein. In another aspect, the central computer system 43 includes multiple receivers arranged at different locations to receive the temperature message St and the label message $S_{ID}$ from different patients, and a host of the central computer system 43 is electrically connected to these receivers.

When the received temperature message St indicates that the body temperature exceeds a predetermined range, the central computer system 43 generates a warning message Sw associated with the label message $S_{ID}$, wherein said associated with the label message $S_{ID}$ is referred to that the warning message Sw is dedicated to a human body who wears the wearable accessory 41 that sends the label message $S_{ID}$ so as to avoid the confusion between patients. In one aspect, the warning message Sw is represented by a lamp or a broadcast. In another aspect, the central computer system 43 further includes a transmitter (not shown) for wirelessly sending the warning message Sw to a portable device 49, which is carried by or assigned to a medical staff.

In one non-limiting aspect, the central computer system 43 further includes a display 431 (e.g., LCD or plasma) for showing a temperature distribution with time of the body temperature to be watched by the medical staff. The display 431 shows or is marked a high temperature threshold TH1 and a low temperature TH2 on the screen thereof. When identifying that the body temperature detected by the thermal sensor 411 exceeds a predetermined range (e.g., higher than TH1 or lower than TH2), the central computer system 43 generates the warning message Sw. The thresholds TH1 and TH2 may be set or adjusted corresponding to different users.

In one non-limiting aspect, the central computer system 43 further includes a camera 45. When identifying that the body temperature exceeds the predetermined range, the central computer system 43 turns on the camera 45 to perform the patient monitoring. In normal time, the camera 45 is turned off to protect the privacy of the patient. Furthermore, images acquired by the camera 45 are selected to be shown on the display 431.

In one non-limiting aspect, the central computer system 43 further includes a dosing equipment 47. When identifying that the body temperature exceeds the predetermined range, the central computer system 43 turns on the dosing equipment to perform the automatic dosing. The operating status of the dosing equipment 47 is selected to be shown on the display 431 if it is included. The display 431 further shows the relationship between the dosage and the variation of body temperature. The central computer system 43 further controls the dosing equipment 47 to stop dosing when the body temperature recovers to be within the predetermined range.

Although in the above embodiment the medical monitoring system 400 is applied to an operation organization, the present disclosure is not limited thereto. The medical monitoring system 400 of the third embodiment is also applicable to a home caring system, and the operation of the central computer system 43 is replaced by a tablet computer, a desktop computer or a notebook computer.

Although the third embodiment is described using a wearable accessory 41, it is only intended to illustrate but not to limit the present disclosure. In other aspects, the wearable accessory 41 is replaced by a monitoring device that is not directly attached to a human body. The thermal sensor 411 detects the body temperature by non-contacting the human body.

Figure 5:
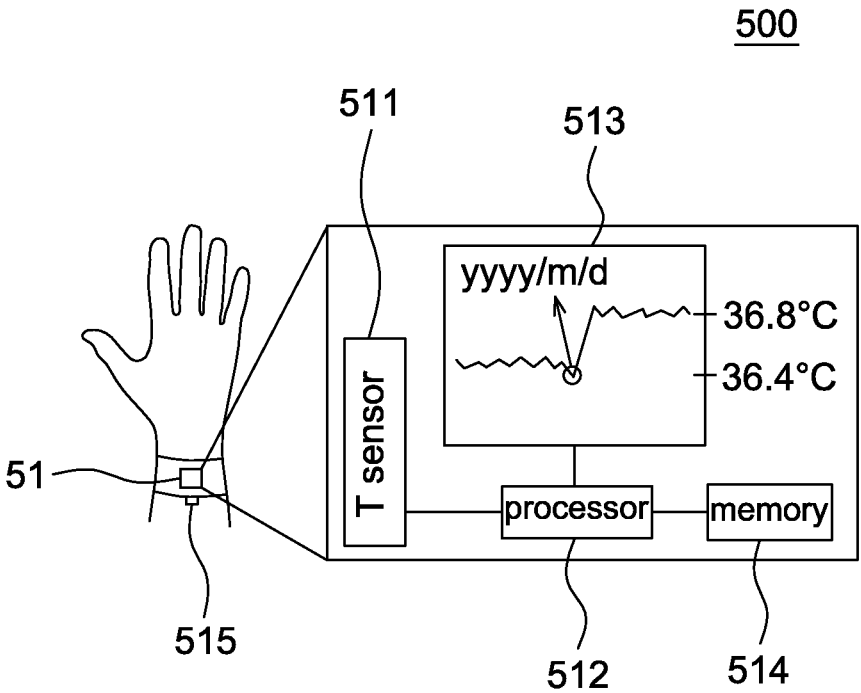
FIG. 5 is a schematic diagram of a body temperature monitoring device according to a fourth embodiment of the present disclosure.

Referring to FIG. 5, it is a schematic diagram of a body temperature monitoring device 500 according to a fourth embodiment of the present disclosure. The body temperature monitoring device 500 includes a wearable accessory 51, a thermal sensor (shown as T sensor) 511, a processor 512, a display 513 and a memory 514. The processor 512 is also a DSP, MCU, CPU, ASIC, GPU or the like.

The wearable accessory 51 is worn on a human body. For example, the wearable accessory 51 is a watch, a bracelet or an armband without particular limitations as long as it is a device attached to and fixed on a skin surface. The thermal sensor 511 is disposed in the wearable accessory 51 and used to detect a basal body temperature (BBT) of a human body, and output an electrical signal or a digital signal to the processor 512. The processor 512 is used to record the BBT every day, and controls the display 513 to give a hint when a temperature variation of the BBT exceeds a temperature variation threshold (e.g., 0.3 to 0.5 degrees which is previously stored in the memory 514).

For example, the processor 512 controls the thermal sensor 511 to measure the BBT at a fixed time of a day every day, e.g., based on a system clock. Or, the body temperature monitoring device 500 further includes a button 515, and when receiving a pressed signal of the button 515, the processor 512 controls the thermal sensor 511 to measure the BBT to be shown on the display 513 and stored in the memory 514 for the long term monitoring.

The display 513 gives various messages using a diagram or numbers, e.g., showing the message including an ovulatory phase or date (e.g., shown by yyyy/m/d), a high temperature interval (e.g., FIG. 5 showing days of BBT at about 36.8 degrees, which is determined according to different users) and a low temperature interval (e.g., FIG. 5 showing days of BBT at about 36.4 degrees, which is determined according to different users) to help the user to know her menstrual period.

Preferably, the BBT is measured when a user wakes up but does not leave the bed yet. Accordingly, to achieve the automatic measurement, the body temperature monitoring device 500 further includes an acceleration detection device (e.g., G-sensor) for detecting whether a user gets out of bed. For example, the acceleration detection device only detects accelerations in two dimensions (e.g., XY axes) before the user gets up, and further detects an acceleration in a third dimension (e.g., Z-axis acceleration) after the user gets up. The processor 512 is further used to identify a wake up time (not leaving bed yet) according to the detected acceleration value of the acceleration detection device, and controls the thermal sensor 511 to automatically detect the BBT at the wake up time. Herein, said detecting an acceleration is referred to that an acceleration value larger than a predetermined threshold is detected.

In one non-limiting aspect, when detecting a user is lying on a bed (e.g., not detecting Z-axis acceleration or other acceleration within a predetermined time interval), the processor 512 controls the thermal sensor 511 to measure a temperature once every a predetermined interval (e.g., one to several minutes). Only the detected temperature before a Z-axis acceleration being detected is taken as the BBT by the processor 512 and stored in the memory 514. To improve the detecting accuracy, if the processor 512 does not detects another Z-axis acceleration within a predetermined time interval after one Z-axis acceleration has been detected, it means that the user only changes a lying posture on the bed and thus the measured temperature temporarily being stored is not considered as the BBT.

In one non-limiting aspect, the temperature monitoring device 500 is further wirelessly coupled to another thermal sensor that includes a wireless transceiver and a processor (e.g., DSP). Said another thermal sensor is arranged near the user or bed. When the temperature monitoring device 500 detects a Z-axis acceleration, a request signal is sent to said another thermal sensor, and the processor of said another thermal sensor recognizes (using hardware and/or software therein to identify a variation of high temperature region in the acquired data) whether the user gets up. If the user gets up, said another thermal sensor sends a response signal to the temperature monitoring device 500 to cause the temperature monitoring device 500 to use a body temperature measured before leaving the bed as the BBT. If the user does not get up, said another thermal sensor does not send a response signal or sends a response signal indicating that it is not necessary to measure a body temperature.

In one non-limiting aspect, when detecting a user shaking the temperature monitoring device 500 in a predetermined pattern (e.g., up-down shaking or left-right shaking for several times), the processor 512 starts to measure a body temperature and records the measured temperature as the BBT.

It is appreciated that numbers mentioned in the above embodiments are only intended to illustrate but not to limit the present disclosure.

It should be mentioned that although the recognition system 100 mentioned above is illustrated to include both the thermal sensor 11 and the image sensor 12, the present disclosure is not limited thereto. In other embodiments, the recognition system 100 includes one of the thermal sensor 11 and the image sensor 12, and receives another signal (e.g., image frame Im or thermal image Ih) from an external sensor via an I/O interface thereof. For example, the recognition system 100 includes the thermal sensor 11 but receives the image frame Im from an external image sensor; or the recognition system 100 includes the image sensor 12 but receives the thermal image Ih from an external thermal sensor.

Figure 6:
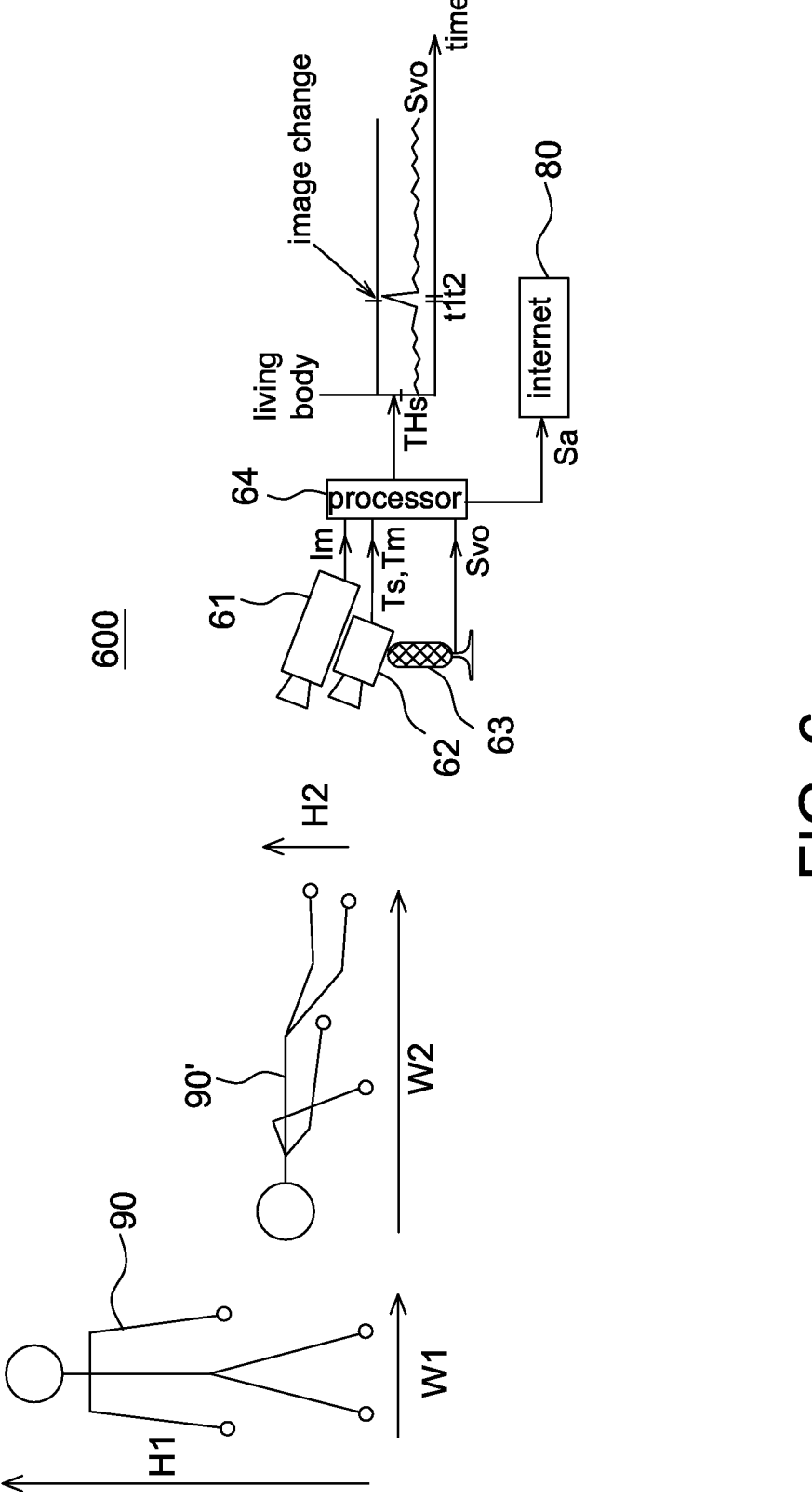
FIG. 6 is a schematic diagram of a falling detection system according to a fifth embodiment of the present disclosure.

Please refer to FIG. 6, it is a schematic diagram of a falling detection system 600 according to a fifth embodiment of the present disclosure, in which a reference number 90 indicates a standing state of a human, and a reference number 90' indicates a falling state of a human.

The falling detection system 600 includes an image sensor 61, a thermal sensor 62 (e.g., a single-pixel thermal sensor or a thermal sensor array including multiple pixels), a microphone 63 and a processor 64. The image sensor 61, the thermal sensor 62 and the processor 64 have been described in the above embodiments, and thus details thereof are not repeated herein. The microphone 63 is any type of voice receiving device that transfers sound being detected to a voice signal Svo, which is then outputted to the processor 64.

The image sensor 61 is used to output image frames Im at a predetermined frame rate to the processor 64. The thermal sensor 62 is used to output thermal signals Ts (e.g., when a single-pixel thermal sensor being adopted) or thermal images Tm (e.g., when a thermal sensor array being adopted) at a predetermined frequency to the processor 64. The processor 64 is coupled to the image sensor 61, the thermal sensor 62 and the microphone 63, and is embedded with algorithms and codes to process, e.g., using hardware and/or firmware, signals received from the image sensor 61, the thermal sensor 62 and the microphone 63. Preferably, the image sensor 61 and the thermal sensor 62 have substantially identical field of views in the detection region of the falling detection system 600 such that the same object is captured by the image sensor 61 and the thermal sensor 62 with corresponding features.

Figure 7:
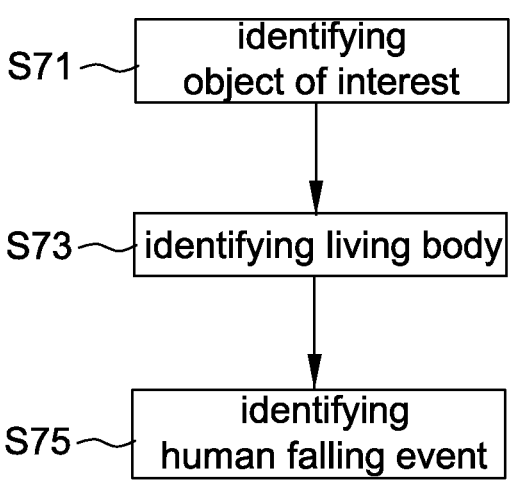
FIG. 7 is a flow chart of an operating method of the falling detection system in FIG. 6.

Please refer to FIG. 7, it is a flow chart of an operating method of the falling detection system 600 in FIG. 6, including the steps of: identifying an object of interest (Step S71); identifying a living body (Step S73); and identifying a human falling event (Step S75).

In the fifth embodiment, when a human falling event is identified, the processor 64 is arranged to transmit an alarm signal Sa via an internet system 80 to a preset device, which is a computer system (e.g., a smartphone, notebook computer, a tablet computer, a desktop computer, a work station or the like) connected to the falling detection system 600 via the internet system 80, and the preset device preferably has a screen for being watched by any person (e.g., a relative, a medical staff, a care worker or the like) who is interested in the falling detection result of the falling detection system 600. The information of the preset device is previously recorded in the falling detection system 600. In another aspect, the processor 64 is further arranged to transmit image frames Im acquired by the image sensor 61 to the preset device via the internet system 80 after receiving a requirement from the preset device via the internet system 80. In a further aspect, the falling detection system 600 directly gives an alarm sound, light, vibration when a human falling event is identified.

Step S71: Firstly, the falling detection system 600 identifies an object of interest (e.g., a person 90 in FIG. 6). The object of interest is identified according to at least one of the image frame Im and the thermal image Tm (in the case a thermal sensor array being adopted).

In one aspect, the processor 64 confirms an object of interest according to face recognition on an object image (e.g., image of 90) in the image frame Im. Once a human face is recognized in the image frame Im, the object of interest is confirmed and tagged by the processor 64 for continuous tracking.

In another aspect, the processor 64 confirms an object of interest according to a height-width ratio (e.g., H1/W1 in FIG. 6) of an object image (e.g., image of 90) in the image frame Im. Once the object image has a height-width ratio within a predetermined ratio range, the object of interest is confirmed and tagged by the processor 64 for continuous tracking.

In a further aspect, the processor 64 confirms an object of interest according to a height-width ratio (e.g., H3/W3 in FIG. 8, which shows thermal images Tm1 and Tm2 acquired by a thermal sensor array 62) of a thermal object image Tm_90 in the thermal image Tm corresponding to the object image (e.g., image of 90) in the image frame Im. Once the thermal object image has a height-width ratio within a predetermined ratio range, the object of interest is confirmed and tagged by the processor 64 for continuous tracking.

That is, in the fifth embodiment, an object of interest is identified according to at least one of face recognition, a height-width ratio of an object image (e.g., image of 90) in the image frame Im and a height-width ratio of a thermal object image Tm_90 in the thermal image Im. The face recognition and recognition of height-width ratio are respectively performed using a human face model and a height-width ratio model previously constructed by machine learning.

Step S73: Then, the processor 63 identifies whether an object of interest is a living body or not according to the thermal signal Ts or the thermal image Tm. For example, when the thermal signal Ts or the thermal image Tm indicates a temperature of the object of interest is between 35° C. and 40° C., the processor 64 identifies that the object of interest is a living body. The method of identifying an object temperature based on signals of a thermal sensor 62 is known to the art and thus details thereof are not described herein.

In one aspect, the Steps S71 and S73 are performed at the same time. For example, the processor 64 determines an object of interest when an object image (e.g., image of 90) in the image frame Im is identified as a living body according to a thermal object image Tm_90 in the thermal image Tm corresponding to the object image. More specifically, identifying a living body is used as the fourth condition (besides the three conditions mentioned above) to identify an object of interest. In this aspect, the processor 64 uses at least one of four conditions to confirm an object of interest.

In the present disclosure, if the object of interest is not identified as a living object, the operating method does not move to the Step S75.

Step S75: Finally, the processor 64 identifies a human falling event according to whether matching between a time stamp of image change in the image frame Im and/or in the thermal image Tm and an abrupt sound (e.g., occurring at time point t2 in FIG. 6) in the voice signal Svo is true or not. In the present disclosure, the abrupt sound is, for example, a sound having intensity higher than a sound threshold (e.g., THs shown in FIG. 6), or a sound having a predetermined voice print (previously recorded in the falling detection system 600) or having a predetermined words and phrases, optionally with intensity higher than a sound threshold.

Herein, the matching is referred to the abrupt sound occurs within a predetermined time interval behind a time stamp (e.g., occurring at time point t1 in FIG. 6) of the image change. It should be mentioned that in the case that a space being monitored by the falling detection system 600 of the present disclosure is not very large, the time point t1 is very close to the time point t2, and different time points shown in FIG. 6 are only intended to illustrate but not to limit the present disclosure. When the matching between the time stamp of image change and the abrupt sound in the voice signal Svo is confirmed, a human falling event is identified by the processor 64.

In one aspect, an image change is a height-width ratio change of the object image in successive image frames Im associated with the object of interest identified in the previous steps. As shown in FIG. 6, when the height-width ratio changes from (H1/W1 of 90) to (H2/W2 of 90'), the image change is confirmed. In the present disclosure, (H1/W1) and (H2/W2) are respectively within a predetermined range previously determined based on statistics or machine learning.

Figure 8:
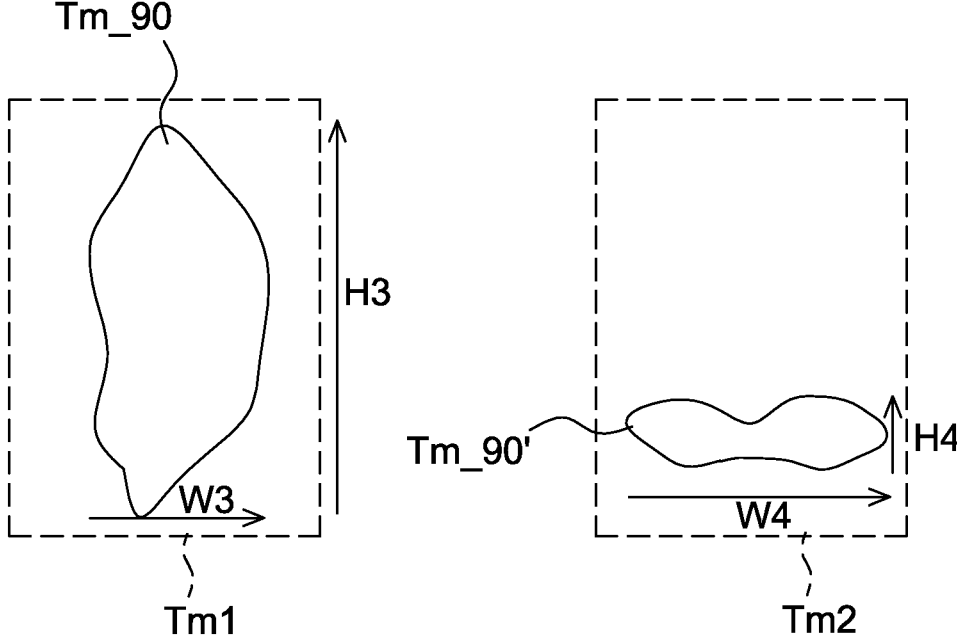
FIG. 8 is a schematic diagram of the image change detected by the falling detection system in FIG. 6.

In another aspect, an image change is a height-width ratio change of the thermal object image in successive thermal images Tm associated with the object of interest identified in the previous steps. As shown in FIG. 8, when the height-width ratio changes from (H3/W3 of Tm_90) to (H4/W4 of Tm_90'), the image change is confirmed. In the present disclosure, (H3/W3) and (H4/W4) are respectively within a predetermined range previously determined based on statistics or machine learning.

In a further aspect, an image change is a face position change of the object image in successive image frames Im associated with the object of interest identified in the previous steps. As shown in FIG. 6, when the face position changes from (H1 of 90) to (H2 of 90'), the image change is confirmed. In the present disclosure, (H1) and (H2) are respectively within a predetermined range previously determined based on statistics or machine learning.

More specifically, the image change herein includes at least one of a height-width ratio change of the object image in successive image frames Im, a height-width ratio change of the thermal object image in successive thermal images Tm and a face position change of the object image in successive image frames Im according to different arrangements. If more than one image changes are used, the time stamps of these image changes are required to match a time point that an abrupt sound occurs in order to confirm a human falling event.

In one aspect, a human falling event is confirmed after a predetermined waiting time that the matching between the image change and the abrupt time occurs to reduce the false alarm. For example, when the object image changes from (H2/W2) back to (H1/W1) or the thermal object image changed from (H4/W4) back to (H3/W3) within the predetermined waiting time, the human falling event is not identified or approved, and the alarm signal Sa is not sent because the condition may not need to be reported.

In one aspect, in order to reduce the power consumption and the interference, the microphone 63 is turned on only when the living body is identified.

In another aspect, the processor 64 determines a region of interest WOI in an thermal image Tm acquired by a thermal sensor array 62 (similar to the second embodiment), and performs human falling detection according to an image region in an image frame Im captured by the image sensor 61 corresponding to the region of interest WOI determined in the thermal image Tm. Information outside the corresponding image region is not used in the human falling detection. As mentioned above in the fifth embodiment, the processor 64 determines that a human falling event occurs according to the matching between an image change and an abrupt sound occurrence.

It should be mentioned that although FIG. 6 shows that the image sensor 61, the thermal sensor 62 and the microphone 63 are three individual components, it is only intended to illustrate but not to limit the present disclosure. In another aspect, at least two of the image sensor 61, the thermal sensor 62 and the microphone 63 are arranged in the same camera device.

As mentioned above, the recognition system and monitoring system using only the image sensor has its operational limitation such that a complicated algorithm has to be used to overcome this limitation. Accordingly, the present disclosure further provides a face recognition system, (e.g., FIG. 2A), a gesture recognition system (e.g., FIG. 3A), a medical monitoring system (e.g., FIG. 4) and a body temperature monitoring device (e.g., FIG. 5) that overcome the limitation of a system using only the image sensor by employing a temperature sensor to effectively improve the accuracy of a recognition system and broaden the adaptable scenario of a monitoring system.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. A falling detection system, comprising:
an image sensor, configured to output an image frame;
a thermal sensor, configured to output a thermal image;
a microphone, configured to output a voice signal; and
a processor, coupled to the image sensor, the thermal sensor and the microphone, and configured to
tag an object image in the thermal image as an object of interest for continuous tracking upon a height-width ratio of the object image being within a predetermined ratio range,
after the object of interest is tagged, identify whether the object of interest is a living body or not according to the thermal image,
identify a height-width ratio change in the height-width ratio of the object of interest upon the object of interest being identified as the living body, and
identify whether a time stamp of the height-width ratio change matches a time point of an abrupt sound occurring in the voice signal.

2. The falling detection system as claimed in claim 1, wherein in response to the thermal image indicating a temperature of the object of interest between 35° C. and 40° C., the processor is configured to identify that the object of interest is the living body.

3. The falling detection system as claimed in claim 1, wherein in response to the abrupt sound occurring within a predetermined time interval behind the time stamp of the height-width ratio change, the processor is configured to identify a human falling event.

4. The falling detection system as claimed in claim 3, wherein the processor is further configured to transmit an alarm signal via an internet system to a preset device upon the human falling event being identified.

5. The falling detection system as claimed in claim 4, wherein the processor is further configured to transmit image frames acquired by the image sensor to the preset device via the internet system after receiving a requirement from the preset device via the internet system.

6. The falling detection system as claimed in claim 1, wherein the abrupt sound is
a sound having intensity higher than a sound threshold, or
a sound having a predetermined voice print and having intensity higher than a sound threshold.

7. The falling detection system as claimed in claim 1, wherein the microphone is turned on only in response to the living body being identified.

8. The falling detection system as claimed in claim 1, wherein recognition of the height-width ratio is performed using a height-width ratio model previously constructed by machine learning.

9. A falling detection system, comprising:
an image sensor, configured to output an image frame;
a thermal sensor array, configured to output a thermal image;
a microphone, configured to output a voice signal; and
a processor, coupled to the image sensor, the thermal sensor array and the microphone, and configured to perform a falling detection by
tagging an object as an object of interest for continuous tracking upon a human face being recognized by face recognition in the image frame and upon a height-width ratio of a thermal object image in the thermal image corresponding to the human face is within a predetermined ratio range, after the object of interest is tagged, identifying whether the object of interest is a living body or not according to the thermal object image in the thermal image, identifying a height-width ratio change in the height-width ratio of the thermal object image in the thermal image associated with the object of interest upon the object of interest being identified as the living body, and identifying whether a time stamp of the height-width ratio change matches a time point of an abrupt sound occurring in the voice signal.

10. The falling detection system as claimed in claim 9, wherein in response to the thermal image indicating a temperature of the object of interest between 35° C. and 40° C., the processor is configured to identify that the object of interest is the living body.

11. The falling detection system as claimed in claim 9, wherein in response to the abrupt sound occurring within a predetermined time interval behind the time stamp of the height-width ratio change, the processor is configured to identify a human falling event, and the processor is further configured to transmit an alarm signal via an internet system to a preset device upon the human falling event being identified.

12. The falling detection system as claimed in claim 9, wherein the processor is further configured to firstly determine a region of interest, which has a temperature larger than a temperature threshold, in the thermal image, then perform the falling detection according to an image region in the image frame corresponding to the determined region of interest, wherein the image region is obtained from the determined region of interest using a previously determined space conversion algorithm between the thermal image and the image frame.

13. The falling detection system as claimed in claim 9, wherein the processor is further configured to identify the object of interest according to another height-width ratio of the object image in the image frame.

14. The falling detection system as claimed in claim 13, wherein the processor is further configured to identify another height-width ratio change of the object image in the image frame associated with the object of interest upon the object of interest being identified as the living body.

15. The falling detection system as claimed in claim 14, wherein the processor is further configured to identify whether another time stamp of the another height-width ratio change matches the time point of the abrupt sound occurring in the voice signal.

16. The falling detection system as claimed in claim 15, wherein in response to the abrupt sound occurring within a predetermined time interval behind the time stamp and the another time stamp, the processor is configured to identify a human falling event.

17. The falling detection system as claimed in claim 16, wherein the processor is further configured to transmit an alarm signal via an internet system to a preset device upon the human falling event being identified.

18. The falling detection system as claimed in claim 9, wherein the abrupt sound is a sound having intensity higher than a sound threshold, or a sound having a predetermined voice print and having intensity higher than a sound threshold.

19. The falling detection system as claimed in claim 9, wherein the microphone is turned on only in response to the living body being identified.

20. A falling detection system, comprising:

an image sensor, configured to output an image frame;

a thermal sensor array, configured to output a thermal image;

a microphone, configured to output a voice signal; and a processor, coupled to the image sensor, the thermal sensor array and the microphone, and configured to tag a thermal object image in the thermal image as an object of interest for continuous tracking upon a height-width ratio of the thermal object image being within a predetermined ratio range when an object image in the image frame is identified as a living body according to the thermal object image in the thermal image corresponding to the object image having a temperature between 35° C. and 40° C., and identify a human falling event according to a time point of an abrupt sound in the voice signal in conjunction with at least one of a face position change of the object image in successive image frames acquired by the image sensor and a height-width ratio change of the thermal object image in successive thermal images acquired by the thermal sensor array.

\* \* \* \* \*